United States Patent [19]

Villaveces

[11] Patent Number: 4,852,844
[45] Date of Patent: Aug. 1, 1989

[54] DEVICE FOR AIDING IN PREPARATION OF INTRAVENOUS THERAPY

[76] Inventor: James W. Villaveces, 88 Eugenia Dr., Ventura, Calif. 93003

[21] Appl. No.: 185,963

[22] Filed: Apr. 25, 1988

[51] Int. Cl.$^4$ ............................................. A61M 5/32
[52] U.S. Cl. .................................. 248/314; 248/316.7; 604/192; 604/263
[58] Field of Search ............... 248/534, 537, 538, 539, 248/205.1, 205.3, 205.4, 205.2, 359 R, 108, 359 A, 360, 312, 312.1, 313, 65, 74.1, 74.2, 309.1, 314, 316.7, 316.1, 121; 604/192, 187, 263; 206/365, 366, 380

[56] References Cited

U.S. PATENT DOCUMENTS

| | | | |
|---|---|---|---|
| 1,053,255 | 2/1913 | Ward | 248/538 |
| 3,304,039 | 2/1967 | Edelman | 248/108 |
| 3,370,818 | 2/1968 | Perr | 248/205.2 |
| 4,239,167 | 12/1980 | Lane | 248/205.3 |
| 4,375,849 | 3/1983 | Hanifl | 206/366 |
| 4,429,793 | 2/1984 | Ehmann | 206/366 |
| 4,485,918 | 12/1984 | Mayer | 206/380 |
| 4,573,576 | 3/1986 | Krol | 206/366 |
| 4,596,562 | 6/1986 | Vernon | 604/192 |
| 4,623,336 | 11/1986 | Pedicano | 604/263 |
| 4,717,386 | 1/1988 | Simmons | 604/263 |
| 4,737,149 | 4/1988 | Gillilan | 604/192 |

FOREIGN PATENT DOCUMENTS

| | | | |
|---|---|---|---|
| 2740335 | 9/1977 | Fed. Rep. of Germany | 206/366 |
| 3433359 | 4/1986 | Fed. Rep. of Germany | 604/263 |
| 2198644 | 6/1988 | United Kingdom | 604/192 |

Primary Examiner—Ramon O. Ramirez
Assistant Examiner—Robert A. Olson
Attorney, Agent, or Firm—Milton S. Gerstein

[57] ABSTRACT

A device for aiding a nurse in the preparation and set-up of intravenous therapy. The device has a backing plate with a backing layer of adhesive for securement to an IV pole, the backing plate being made of a flexible material so that it may be wrapped about the IV pole. A frustro-conical hollow member is supported by the front surface of the backing plate in which are provided friction-gripping ribs to firmly hold and grip a needle-cap of an intravenous needle, so that, when the needle and its cap are inserted into the hollow the cap is firmly held, after which the needle proper may be removed from the cap for subsequent IV therapy. The device allows a nurse to accomplish such needle and cap separation with only one hand, to free her other hand to hold another part of the IV set-up or to perform another task.

13 Claims, 2 Drawing Sheets

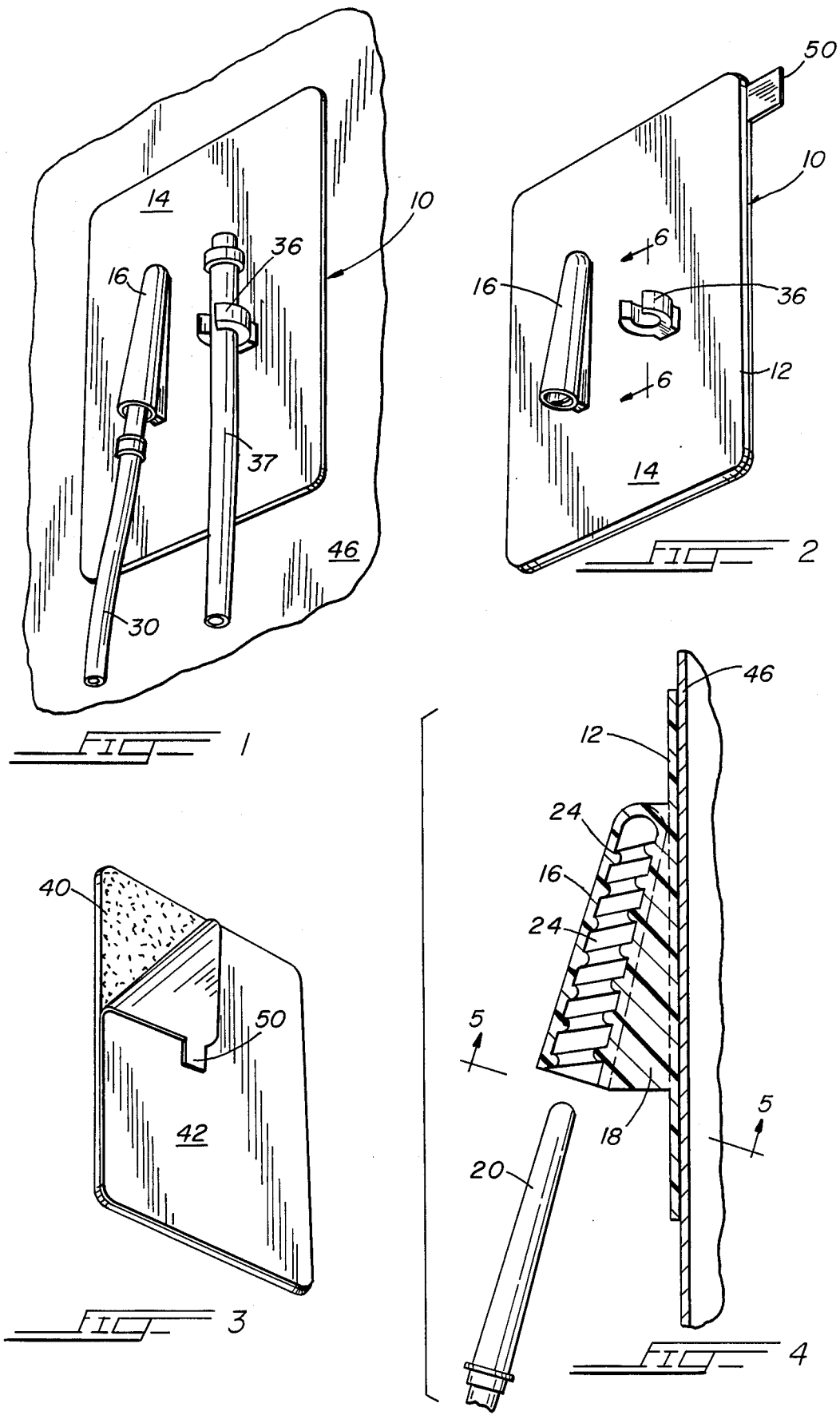

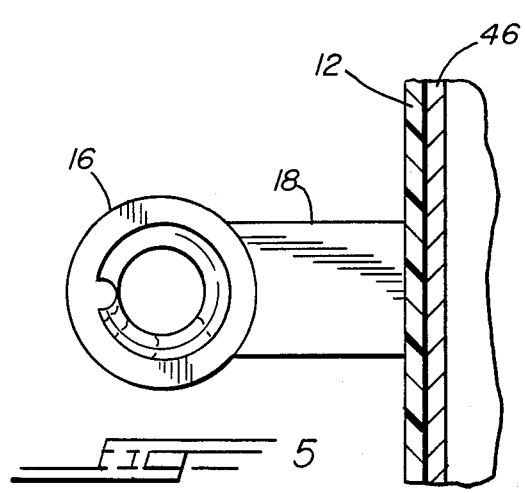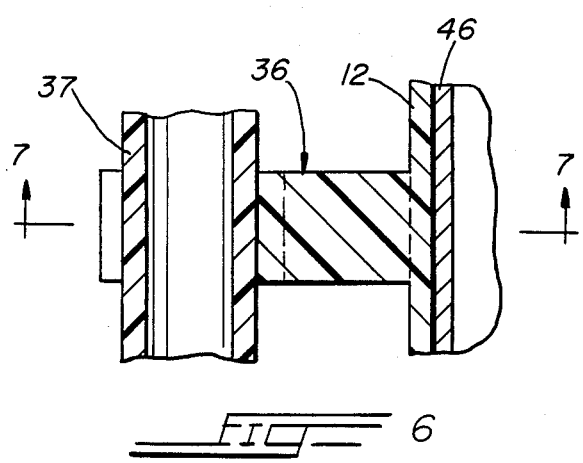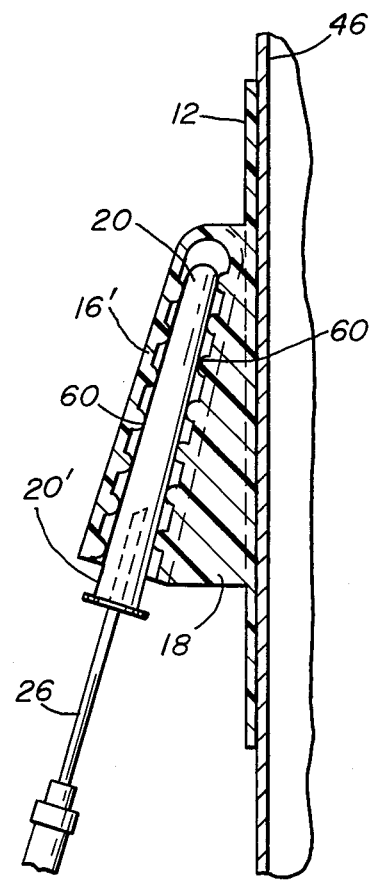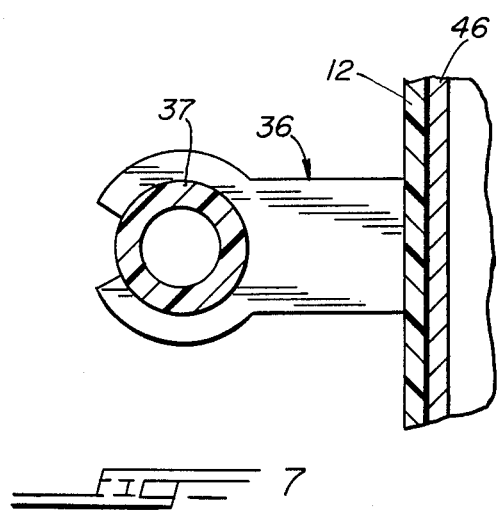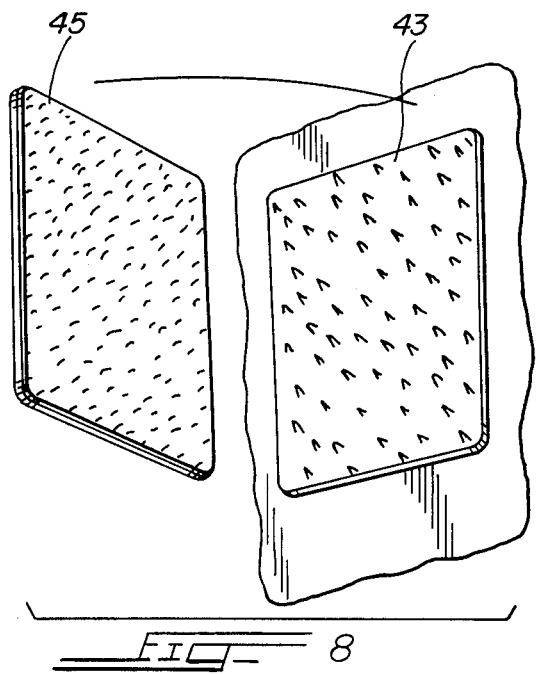

DEVICE FOR AIDING IN PREPARATION OF INTRAVENOUS THERAPY

BACKGROUND OF THE INVENTION

The present invention is directed to a device that aids a nurse in the preparation of setting up intravenous therapy. At least ten million of the more than forty million Americans hospitalized each year receive some form of intravenous therapy, such as blood transfusion, fluid and electrolyte replacement or total parental nutrition. Many things may go wrong with such therapy, such as, for example, sepsis. In effect, the IV is a conduit through the protective skin for an infection, which, therefore, must be guarded against. Any such tube inserted into the body, whether IV, nasogastric feeding, intra-arterial monitoring line or urinary catheter, deserves a maximum in antiseptic technique. Yet, proof is extant showing that hospital personnel are often delinquent in meeting necessary sanitary and hygenic precautions. Studies have found that 8% of nosocomial (hospital-acquired) infections are ascribed to use of intravascular lines. This translates into an estimated 50,000 device-related septisemias in the United States each year. Of 97 nosocomial epidemics in the world literature between 1965 and 1978, fully ⅓ derived from infusion therapy. Cultures done on catheter or needle used in IV therapy are positive for bacterial isolation in 33% of infusions during the first 12 hours of infusion. Studies have shown the link between thrombophlebitis in patients to the bacterial contamination which has been ascribed to non-aseptic techniques during cannula insertion. It is also a common problem to have nurses use unsanitary techniques in the handling of infiltrated IV lines and clot-blocked IV catheters, as well as catheter-bags needing emptying.

Nurses must set up IV solutions, lines, and needles, and to connect them all before attempting to insert the needle and cannula through the skin, and often have no assistants. Thus, they are forced to take short cuts because of time constraints. It is common for a nurse to remove the cap of a needle with her teeth, then reinsert the needle into the cap held between the teeth. Nurses are also wont to drop tubings, which are left to swing in the air, while the nurse clears a blocked line with a syringe, after which clearing, the tubing is reinserted in the needle or catheter. Ofttimes, the tubing is held under the armpit or draped over the IV pole while the needle or catheter is checked. The problem is, simply, that the nurse has too many tasks to perform in such a short time. She must hold the needle, syringe, tubing, caps and tape when the various IV procedures are undertaken. To replace the IV tubing everytime the line infiltrates or is blocked is not cost effective, which also leads to potential contamination at tubing-ends and cannula ends.

SUMMARY OF THE INVENTION

It is, therefore, the primary objective of the present invention to provide a device by means of which greater care and hygiene may be achieved during the setting up and administering of an intravenous unit as well as during the maintenance thereof.

It is an objective of the present invention to provide a unit that provides a location for use by a nurse when setting up intravenous feeding, and the like, that will temporary hold portions of the IV system, in order to free one of her hands in order to perform another task necessary for the IV installation, preparation, maintenance or removal.

It is an objective of the present invention to provide such a unit that, specifically, temporary holds the cap of the IV needle or catheter, and which may be used for removing the cap from the needle with the use of only one hand during initial IV installation.

It is an objective of the present invention to also provide such a unit that will hold the end of the IV tubing during initial set-up as well as during removal.

Toward these and other ends, the unit of the present invention, in a first embodiment, is a plate-like member having a backing of adhesive or a half of a hook-and-pile fastener, which backing or plate itself is flexible in order to wrap it around a conventional IV post or pole. The plate includes on its front surface face an angularly-mounted, conically-shaped, hollow tube into which is inserted an IV needle or catheter with its cover cap thereon. The interior surface of the hollow tube is provided with a spiral rib extending approximately the entire length of the tube, so that, upon the insertion of the needle and its cover cap into the conically-shaped hollow tube, the needle cover cap is held therein by the static friction provided via the spiral rib, so that the needle may be easily removed from the cover cap. The entire procedure of placing the needle and its cap into the tube and the removal of the needle therefrom and from its associated cap is accomplished with one hand, to thus free the the nurse's other hand for other needed tasks in setting up and preparing the IV, or the like. The front surface face of the plate is also provided with a C-clamp, or the like, for holding the end of the IV tubing with its attached cover for accomplishing the removal of that cover from the tube-end also by one hand. The C-clamp is also useful in temporarily holding any tube during set-up, maintenance, infiltration or withdrawal, such as feeding tubes, suction tubes; urine drainage tubes, and the like.

BRIEF DESCRIPTION OF THE DRAWING

The invention will be more readily understood with reference to the accompanying drawing, wherein:

FIG. 1 an isometric view showing the device for aiding the preparation of intravenous therapy of the invention attached to a post or pole of an IV stand;

FIG. 2 is an isometric view thereof showing the device before securement to the pole;

FIG. 3 is a rear isometric view showing the peelable backing layer of the unit of the invention for exposing the adhesive for securement of the unit to an IV pole;

FIG. 4 is a longitudinal cross-sectional view of the frustro-conical holder for the removal of the needle-cap having a spiral-shaped interior rib for gripping a needle-cap;

FIG. 5 is a view taken along line 5—5 of FIG. 4;

FIG. 6 is a view taken along line 6—6 of FIG. 2;

FIG. 7 is a cross-sectional view taken along line 7—7 of FIG. 6;

FIG. 8 is an isometric view showing the adhesive backing layer exposed after removal of the protective sheet; and FIG. 9 is a modification of the unit of the invention with the frustro-conical holding tube for the needle-cap being provided with a plurality of interior protuberances for gripping the needle-cap.

DETAILED DESCRIPTION OF THE INVENTION

Referring now to the drawings in greater detail, the unit for aiding in the preparation of intravenous therapy is indicated generally by reference numeral 10. The unit 10 is preferably a disposable product, meant for use only one time or for one patient, after which it is discarded in a sanitary manner. The unit 10 is, therefore, made of any suitable flexible thermoplastic resin material, and is defined by a flat plate member 12 having a front planar surface 14 mounting a downwardly-extending, frustro-conically shaped, hollow, holding tubular element 16, having an open end facing downwardly for the passage therethrough of a needle-cap 20 shown in FIG. 4. The holding tubular element 16 forms an acute angle with respect to the front surface 14, as best seen in FIG. 4, so as to allow for easy insertion of the needle and its cap 20. The element 16 is formed integrally with the face plate 12 and connected to the front surface 14 via a web 18 seen in FIG. 4 that increases in width in the downward direction, in order to establish the acute angular positioning of the element 16. The interior circumferential surface of the element 16 is provided with a spiral rib 24 which provides gripping surfaces along the length of the element 16 by which the needle-cap 20 is gripped, so that after such gripping, the needle or catheter proper 26 (see FIG. 9) may be easily removed from its cap by simply pulling on the associated tubular connections 30 connected to the needle. Needle-caps are generally difficult to remove from its associated needle, manual removal being tedious, time-consuming, and difficult for an average nurse. The element 16 and its spiral rib allow such needle and cap separation to be carried out easily, quickly and with only one hand. The shape of the element 16 is preferably frustro-conical in order to conform to the frustro-conical shape of the needle-cap 20. Alternatively, the element 16 may be cylindrical, with the interior spiral rib forming an interior hollow frustro-conical volume, by having the rib portions thereof project more outwardly from the interior circumferential wall of the element 16 as the spiral progresses upwardly along the interior of the element 16. An additional alternative is simply using such a spiral tubing defining an interior frustro-conical volume that is connected to the front surface 14 via the web 18 directly. The unit 10 also has a C-clamp member 36 which is used to hold the end of an IV tubing, nasogastric tubing, intra-arterial monitoring tube line, urinary catheter tubing 37, and the like, which is used with the needle proper. The C-clamp is also used for holding the cap or cover of the IV tubing, so that the tube-end may be removed from its cap in a manner similar to the needle-cap remover member 16.

The unit 10 is provided with an adhesive backing layer 40 that is exposed after a rear protective sheet 42 is removed. This adhesive layer is used for securing the unit 10 to a portion 46 of an IV pole or unit. Since a typical IV pole is relatively narrow, in the preferred embodiment, the plate 12 is made of a soft thermoplastic resin material that is conventional in order to allow the unit 10 to be wrapped around the outer circumferential surface of the IV pole, with the adhesive layer 40 consummating securement. Cardboard may also be used instead. Instead of the use of an adhesive backing, conventional hook-and-pile fasteners may be used, such having one portion 43 easily securable to the IV pole by a backing of adhesive, with the backing of the unit 10 having the mating portion 45 of the hook-and-pile fastener, as shown in FIG. 8. A tab 50 is also provided in order to allow for the easy peeling away of the protective sheet 42.

FIG. 9 shows a modification of the unit 10 in that the element 16' is the same as the element 16 of the preferred embodiment with the exception of the interior spiral rib having been replaced with simple radially-inwardly projecting beads 60 along the length of the frustro-conically shaped interior volume of the element 16' to provide the frictional gripping surfaces to hold the needle-cap 20. Each bead 60 may also, preferably, be circular.

An alternative version of the present invention is to provide the needle-cap 20 itself with an adhesive strip or a portion of a hook-and-pile fastener by which the needle-cap 20 itself is secured to the IV pole 46 directly via such securement. In this case, the needle-cap 20 would have a rectangular strip of such securing means fixedly attached to an outer circumferential surface portion preferably closer to the open mouth end thereof 20', the outward surface of the strip having the adhesive or portion of the hook-and-pile fastener thereof.

While a specific embodiment of the invention has been shown and described, it is to be understood that numerous changes amnd modifications may be made therein without departing the scope and spirit of the invention as set forth in the appended claims.

What I claim is:

1. A device for aiding a nurse in the preparation of intravenous therapy, and the like, comprising:
   a backing plate having a substantially planar front surface and rear surface;
   means for holding and gripping a needle-cap mounted on said front surface defining a frustro-conically shaped hollow interior into which a needle-cap may be inserted;
   said rear surface of said backing plate having securing means thereon for attaching said backing plate to an IV pole, whereby a needle with its cap may be inserted into said means for holding and gripping to grip the needle-cap, after which the needle proper may be removed from its cap for use in intravenous therapy; and
   a C-clamp means for holding a tube-end mounted to said front surface of said backing plate.

2. The device according to claim 1, wherein said securing means comprises an adhesive layer formed on said rear surface, and a protective, peelable cover sheet for said adhesive layer that is removed when securing said backing plate to an IV pole, or the like.

3. The device according to claim 1, wherein said backing plate is made of a soft, flexible material so that it may be wrapped about an IV pole during securement by said securing means.

4. The device according to claim 1, wherein said securing means comprises hook-and-pile fastening means, a first portion thereof being affixed to said rear surface of said backing plate, and a second portion thereof being affixable to a portion of an IV pole.

5. The device according to claim 1, wherein said means for holding and gripping comprises a frustro-conically shaped hollow member extending downwardly at an acute angle with respect to said front surface, and web means connecting said member to said front surface, said web means increasing in width from its upper end toward its lower end to thereby provide said acute angular mounting of said member; said member having a lower open mouth end and an upper closed end.

6. The device according to claim 5, wherein said member further comprises a spiral rib means integrally formed in said hollow interior for increasing static friction with a needle-cap positioned therein.

7. The device according to claim 1, wherein said backing plate and said means for holding and gripping are formed integrally with each other and are made from a flexible material that allows the wrapping thereof about an IV pole.

8. The device according to claim 7, in combination with an upstanding intravenous pole means, said securing means removably attaching said backing plate to a portion of said pole means.

9. The device according to claim 8, in further combination with an intravenous needle, said needle having a protective closure cap; said cap being held in said means for holding and gripping so that said needle proper may be reinserted into said cap when said cap is held and gripped by said means for holding and gripping.

10. The device according to claim 9, in further combination with an intravenous tube means, said tube means having a tube-end held in said means for holding a tube-end, whereby said tube-end may be stationarily and temporarily positioned during IV set-up, repair, and maintenance.

11. A device for aiding a nurse in the preparation of intravenous therapy, and the like, comprising:
  a backing plate having a substantially planar front surface and rear surface;
  means for holding and gripping a needle-cap mounted on said front surface defining a frustro-conical shaped hollow interior into which a needle-cap may be inserted;
  said rear surface of said backing plate having securing means thereon for attaching said backing plate to an IV pole, whereby a needle with its cap may be inserted into said means for holding and gripping to grip the needle-cap, after which the needle proper may be removed from its cap for use in intravenous therapy;
  means for holding a tube-end mounted to said front surface of said backing plate;
  said backing plate being made from flexible material that allows at least partial wrapping thereof about an IV pole;
  an upstanding intravenous pole means, said securing means removably attaching said backing plate to a portion of said pole means;
  an intravenous needle having a protective closure cap, said cap being held in said means for holding and gripping so that said needle proper may be reinserted into said cap when said cap is held and gripped by said means for holding and gripping; and
  intravenous tube means, said tube means having a tube-end held in said means for holding a tube-end, whereby said tube-end may be stationarily and temporarily positioned during IV set-up, repair and maintenance.

12. The device according to claim 11, wherein said means for holding a tube-end comprises a C-clamp.

13. The device according to claim 11, wherein said means for holding and gripping comprises a frustro-conically shaped hollow member extending downwardly at an acute angle with respect to said front surface, and web means connecting said member to said front surface, said web means increasing in width from its upper end toward its lower end to thereby provide said acute angular mounting of said member; said member having a lower open mouth end and an upper closed end.

* * * * *